United States Patent [19]
Schnabel et al.

[11] 3,993,610
[45] *Nov. 23, 1976

[54] POLYURETHANE FOAM

[75] Inventors: Wilhelm J. Schnabel; Maurice C. Raes, both of Branford, Conn.

[73] Assignee: Olin Corporation, New Haven, Conn.

[*] Notice: The portion of the term of this patent subsequent to Apr. 15, 1992, has been disclaimed.

[22] Filed: Apr. 7, 1975

[21] Appl. No.: 565,490

Related U.S. Application Data

[63] Continuation-in-part of Ser. No. 416,042, Nov. 15, 1973, Pat. No. 3,878,235.

[52] U.S. Cl. .................. 260/2.5 AT; 260/2.5 AN; 260/2.5 AP; 260/77.5 AT; 260/453 AR; 260/453 AM
[51] Int. Cl.² .................. C08G 18/06; C08G 18/14
[58] Field of Search ............... 260/2.5 AT, 2.5 AN, 260/2.5 AP, 77.5 AT, 453 AR, 453 AM

[56] References Cited
UNITED STATES PATENTS

| | | | |
|---|---|---|---|
| 3,255,226 | 6/1966 | McShane | 260/453 AM |
| 3,281,447 | 10/1966 | Knopf et al. | 260/453 AR |
| 3,481,968 | 12/1969 | Ottmann et al. | 260/2.5 AT |
| 3,878,235 | 4/1975 | Schnabel et al. | 260/2.5 AT |

*Primary Examiner*—Donald E. Czaja
*Assistant Examiner*—H. H. Fletcher
*Attorney, Agent, or Firm*—F. A. Iskander; T. P. O'Day

[57] ABSTRACT

Selected chlorine-containing methylene-bridged diaryl diisocyanates are used in the production of polyurethane foam.

14 Claims, No Drawings

POLYURETHANE FOAM

This application is a continuation-in-part of co-pending application Ser. No. 416,042, filed Nov. 15, 1973, now U.S. Pat. No. 3,878,235.

This invention relates to a new and highly select group of chlorine-containing methylene-bridged diaryl diisocyanates and to the use of these diisocyanates in the preparation of polyurethanes.

Various aromatic and aliphatic-aromatic polyisocya-

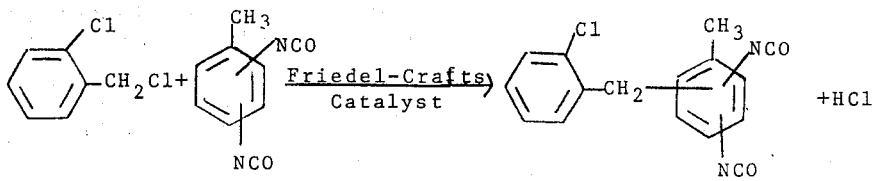

nates have been known for their utility in the production of polyurethane foam. It has also been generally known that flame retardant properties can be achieved in a polyurethane foam by utilizing, in its preparation, a chlorinated polyisocyanate. However, according to the prior art, chlorine-containing aromatic and aliphatic-aromatic polyisocyanates generally are either very viscous liquids or, as is more often the case, solid. As such their use in polyurethane foam production, if at all practicable, entails costly and burdensome handling and processing measures which often render them unfeasible from an economic standpoint. For example, U.S. Pat. No. 3,360,539 discloses that the product of chlorinating an 80/20 isomer mixture of 2,4- and 2,6-toluene-diisocyanate is solid at room temperature. U.S. Pat. No. 2,945,875, which relates to the preparation of monochloro- and dichlorophenylene diisocyanate, again indicates that these chlorinated products are solid at room temperature.

It is further known in the art to prepare certain monomeric methylene-bridged diaryl polyisocyanates by condensing an aromatic or aliphatic aromatic isocyanate with selected aromatic compounds having a halomethyl substituent and which may also have one or more chlorine substituents on the aromatic ring. See U.S. Pat. No. 3,255,226. However, confirming earlier prior art findings, this patent indicates that the products of such condensation reaction are solid or viscous liquids.

Now, according to the invention, a novel and very select group of chlorine-containing methylene-bridged diaryl diisocyanates has been found which are not only liquid but also have a surprisingly low viscosity. These new compounds are identified as o-chlorobenzyl-toluene diisocyanate and dichlorobenzyl-toluene diisocyanate. Pursuant to the invention, they are used to advantage in the preparation of polyurethane foam.

The chlorine-containing diisocyanates of the invention can be prepared by condensing, in the presence of a Friedel-Crafts catalyst, toluene diisocyanate with the appropriate chlorine-substituted benzyl chloride. Thus the o-chlorobenzyl-toluene diisocyanate is obtained by condensing toluene diisocyanate with o-chlorobenzyl chloride in accordance with the following equation:

The dichlorobenzyl-toluene diisocyanate of the invention is similarly prepared by condensing toluene diisocyanate with dichlorobenzyl chloride as illustrated by the following equation:

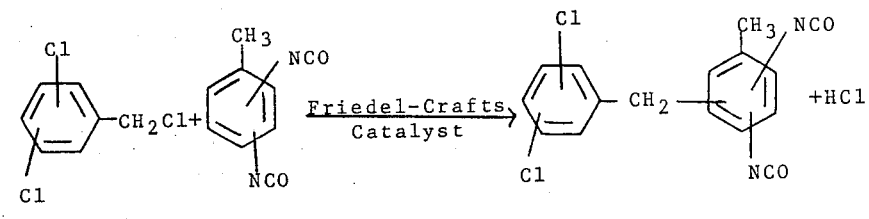

The above-illustrated reactions are carried out at a temperature within the range of 50°–250° C and preferably using a large stoichiometric excess of the toluene diisocyanate. Completion of the reaction is usually signaled when the evolution of hydrogen chloride ceases. A more detailed description of this type of condensation reaction is provided in U.S. Pat. No. 3,255,226, issued June 7, 1966 to H. F. McShane, the entire disclosure of which is incorporated herein by reference.

The toluene diisocyanate reactant which is used to prepare the compounds of the invention can be any isomer or isomer mixture such as 2,4-toluene diisocyanate, 2,5-toluene diisocyanate, 2,6-toluene diisocyanate, 3,5-toluene diisocyanate and mixtures of one or more of these isomers. The preferred toluene diisocyanate isomers are 2,4-toluene diisocyanate, 2,6-toluene diisocyanate, and mixtures of these two isomers. For reasons of economy and commercial availability, a mixture of about 80% by weight of the 2,4-isomer and about 20% by weight of the 2,6-isomer is particularly preferred.

The other reactant used to prepare the diisocyanates of the invention is o-chlorobenzyl chloride or dichlorobenzyl chloride. The latter can be any isomer or mixture of isomers such as 2,3-dichlorobenzyl chloride, 2,4-dichlorobenzyl chloride, 2,5-dichlorobenzyl chloride, 2,6-dichlorobenzyl chloride, and 3,4-dichlorobenzyl chloride.

It is to be noted that the product of either of the two reactions illustrated above is quite often a mixture of isomers which may vary in proportion relative to one another. This has been found to be the case even in the condensation reaction of o-chlorobenzyl chloride with a single toluene diisocyanate isomer. The reason for this is believed to be that there is not a specific carbon atom on the aromatic ring of the toluene diisocyanate which will always become preferentially attached to the methylene bridge provided by the benzyl chloride reactant. Rather, as is more often the case, for every one molecule of benzyl chloride that is condensed with one molecule of toluene diisocyanate, the link could occur via any one of the three available carbons on the aromatic ring of the toluene diisocyanate; and it has been found that the identity and proportion of each isomeric condensation product cannot be uniformly controlled to such a degree as to ascertain the exact isomeric constitution of the total condensation product. For example, in condensing o-chlorobenzyl chloride with 2,4-toluene diisocyanate, the product that is obtained, rather than being a single isomer, is more likely to be a mixture of at least two isomers, namely, a major proportion of 2-chlorophenyl-3'-methyl-4',6'-diisocyanatophenyl-methane, and a lesser proportion of 2-chlorophenyl-2'-methyl-3',5'-diisocyanatophenyl-methane. And of course an even greater number of isomers would result where an isomeric mixture of the toluene diisocyanate reactant is used; or where, in the case of the dichlorobenzyl-toluene diisocyanate, this is prepared from an isomeric mixture of dichlorobenzyl chloride.

Thus it is to be understood that the term "o-chlorobenzyl-toluene diisocyanate", as used in the specification and claims herein, is intended to encompass an isomeric mixture of this compound as well as a single isomer thereof. The same statement of course applies to the term "dichlorobenzyl toluene diisocyanate".

During the course of the reaction of toluene diisocyanate with o-chlorobenzyl chloride or with dichlorobenzyl chloride, by-product hydrogen chloride which is formed may be removed by any suitable means such as by passing a stream of dry nitrogen through the reaction mixture. Thereafter, when the reaction is complete, any unreacted or excess reactants present are removed by distillation. A crude product is thus recovered which usually contains varying proportions of oligomeric materials which are formed as by-products. This crude product is then subjected to fractional distillation in order to recover the o-chlorobenzyl-toluene diisocyanate or the dichlorobenzyl-toluene diisocyanate in purified form. However, in accordance with one embodiment of the invention, the crude product may be used as is in the production of polyurethane foam. For example, in the case of the preparation of o-chlorobenzyl-toluene diisocyanate, the crude reaction product may contain corresponding oligomeric materials which vary in structure and molecular weight. It is believed that these materials have the following structural formula

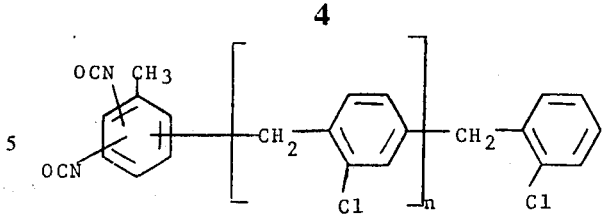

wherein $n$ is an integer of 1 or more. Generally speaking, the presence of these oligomeric materials has not been found to have an adverse effect on the utility of the o-chlorobenzyl-toluene diisocyanate in polyurethane foam production. In fact, their presence may have a desirable effect in certain applications.

The following compounds, and mixtures thereof, are illustrative of the o-chlorobenzyl-toluene diisocyanates of the invention:

2-chlorophenyl-3'-methyl-4',6'-diisocyanatophenyl-methane
2-chlorophenyl-2'-methyl-3',5'-diisocyanatophenyl-methane
2-chlorophenyl-3'-methyl-2',4'-diisocyanatophenyl-methane
2-chlorophenyl-4'-methyl-3',5'-diisocyanatophenyl-methane The following compounds, and mixtures thereof, are illustrative of the dichlorobenzyl-toluene diisocyanates of the invention:

2,4-dichlorophenyl-3'-methyl-4',6'-diisocyanatophenyl-methane
2,4-dichlorophenyl-2'-methyl-3',5'-diisocyanatophenyl-methane
2,5-dichlorophenyl-2'-methyl-3',5'-diisocyanatophenyl-methane
2,4-dichlorophenyl-3'-methyl-2',4'-diisocyanatophenyl-methane
2,5-dichlorophenyl-3'-methyl-2',4'-diisocyanatophenyl-methane
2,4-dichlorophenyl-4'-methyl-3',5'-diisocyanatophenyl-methane
2,5-dichlorophenyl-4'-methyl-3',5'-diisocyanatophenyl-methane
2,5-dichlorophenyl-3'-methyl-4',6'-diisocyanatophenyl-methane
2,3-dichlorophenyl-3'-methyl-4',6'-diisocyanatophenyl-methane The most preferred dichlorobenzyl-toluene diisocyanate of the invention are 2,4-dichlorophenyl-3'-methyl-4',6'-diisocyanatophenyl-methane; 2,4-dichlorophenyl-4'-methyl-3',5'-diisocyanatophenyl-methane; 2,5-dichlorophenyl-3'-methyl-4',6'-diisocyanatophenyl-methane; and mixtures thereof.

Because of its unexpectedly low viscosity, i.e., usually below 110 cps. at 25° C, the preferred chlorinated diisocyanate of the invention is o-chlorobenzyl-toluene diisocyanate as illustrated above. Particularly preferred is the isomeric mixture which is a condensate of o-chlorobenzyl chloride and a mixture of 2,4- and 2,6-toluene diisocyanate.

In addition to their surprisingly low viscosity, the chlorine-containing diisocyanates of the invention are of low volatility and therefore are less toxic than toluene diisocyanate. As such, they are used to advantage, according to the invention, in the production of cellular and noncellular polyurethane. As noted above, the o-chlorobenzyl-toluene diisocyanate, the use of which is preferred, may be employed in purified form or as a crude product of the reaction of toluene diisocyanate with o-chlorobenzyl chloride.

In preparing the polyurethane foam, which may be rigid, flexible, or semi-rigid, conventional foaming techniques may be used such as the one-shot method or the prepolymer technique. However, the one-shot method is generally preferred. The foam is prepared from a reaction mixture which, along with the methylene-bridged diaryl diisocyanates described above, may comprise any combination of polyols including polyether and polyester polyols, foaming agents, catalysts and other reactive and non-reactive ingredients that are useful in the manufacture of polyurethane foam. Typical formulations are described in U.S. Pat. No. 3,072,582, issued Jan. 8, 1963 and Canadian Pat. No. 705,938, issued Mar. 16, 1965.

While, as indicated above, both polyether and polyester polyols can be employed, it is preferred to utilize polyether polyols in the preparation of the polyurethane foam forming reaction mixture. Any suitable polyether polyols, including mixtures thereof, may be used for this purpose. These polyether polyols usually have a hydroxyl number generally ranging from about 25 to about 800.

The polyether polyols include for example oxyalkylated polyhydroxy alcohols having a molecular weight range of about 250–8,000. These oxyalkylated polyhydroxy alcohols are generally prepared by methods well known in the art such as reacting, in the presence of an alkaline catalyst, a polyhydroxy alcohol and an alkylene oxide such as ethylene oxide, propylene oxide, butylene oxide, amylene oxide, epichlorohydrin, and mixtures of these alkylene oxides, using either random or step-wise addition.

Polyhydroxy alcohols suitable for use in preparing the polyether polyols include ethylene glycol, pentaerythritol, methyl glucoside, propylene glycol, 2,3-butylene glycol, 1,3-butylene glycol, 1,5-pentane diol, 1,6-hexane diol, glycerol, trimethylolpropane, sorbitol, sucrose, dextrose, mixtures thereof and the like. If desired, a portion or all of the polyhydroxy alcohol may be replaced with another compound having at least two reactive hydrogen atoms, such as alkyl amines, alkylene polyamines, cyclic amines, amides, and polycarboxylic acids. Suitable alkyl amines and alkylene polyamines include methylamine, ethylamine, propylamine, butylamine, hexylamine, ethylenediamine, 1,6-hexanediamine, diethylenetriamine, and the like. Also, such cyclic amines as piperazine, 2-methylpiperazine and 2,5-dimethylpiperazine can also be used. Amides, such as acetamide, succinamide, and benzensulfonamide, constitute a further class of such reactive hydrogen compounds. A still further class of such reactive hydrogen compounds is the di- and polycarboxylic acids, such as adipic acid, succinic acid, glutaric acid, diglycollic acid, and the like.

Although as indicated above, the polyurethane foams of the invention can be flexible, semi-rigid, or rigid, the flexible foams are preferred. Therefore in preparing the polyurethane foam in accordance with this preferred embodiment of the invention, a polyol is used having a molecular weight of about 2,000–7,000 and more preferably about 2,500–6,000.

The polyurethane foams are prepared in the presence of a foaming agent which may be any one of those known to be useful for this purpose. Illustrative are water and organic foaming agents containing up to about seven carbon atoms such as the halogenated hydrocarbons, lower molecular weight alkanes, alkenes, ethers, and mixtures thereof. Typical halogenated hydrocarbons include, but are not limited to, monofluorotrichloromethane, dichlorofluoromethane, diflurordichloromethane, 1,1,2-trichloro-1,2,2-trifluoroethane, dichlorotetrafluoroethane, ethyl chloride, methylene chloride, chloroform, and carbon tetrachloride. Other useful foaming agents include lower molecular weight alkanes, alkenes and ethers such as methane, ethane, ethylene, propane, propylene, pentane, hexane, heptane, ethyl ether, diisopropyl ether, mixtures thereof, and the like. The amount of foaming agent employed may be varied within a wide range. Generally, however, the halogenated hydrocarbons are employed in an amount from about 1 to about 50, and preferably about 5–35, parts per 100 parts by weight of the polyol, and generally water is employed in an amount from about 1.0 to 6.0 parts by weight per 100 parts by weight of the polyol.

The polyurethane foams are prepared in the presence of a catalytic amount of a reaction catalyst. The catalyst employed may be any one of those known to be useful for this purpose, such as tertiary amines and metallic salts, particularly stannous salts, and mixtures thereof. Typical tertiary amines include, but are not limited to, the following: N-ethyl morpholine, N-hydroxyethyl morpholine, triethylene diamine, triethylamine and trimethylamine. Typical metallic salts include, for example, the salts of antimony, tin and iron, e.g., dibutyltin dilaurate, stannous octoate, and the like. Any catalytic proportion of catalyst or catalyst mixture may be employed such as between about 0.1 and about 3.0 percent, and preferably between about 0.5 and about 2.5 percent, by weight of the polyol.

It is preferred in the preparation of the polyurethane foams of the present invention to employ minor amounts of a conventional surfactant in order to further improve the cell structure of the polyurethane foam. Typical of such surfactants are the silicones, and the siloxaneoxyalkylene block copolymers. U.S. Pat. No. 2,834,748 and T. H. Ferrigno, Rigid Plastic Foams (New York:Reinhold Publishing Corp., 1963) pages 38–42, disclose various surfactants which are useful for this purpose. Generally up to 2 parts by weight of the surfactant are employed per 100 parts of the polyol.

In preparing the polyurethane foam, such proportions of reactants, i.e., polyols and isocyanates, are used as to provide at least about 0.7, and preferably no greater than about 1.25, NCO groups per each hydroxyl group present in the reaction mixture, which includes the polyol as well as any additive or foaming agent that is employed. A particularly preferred range is about 0.9–1.15 NCO groups per hydroxyl group. A polyurethane foam forming mixture comprising the above-described ingredients is charged to a suitable reaction zone such as by pouring into a suitable mold or onto a moving conveyor belt where reaction proceeds. The foaming reaction is exothermic, and auxiliary heat is usually not necessary to effect the reaction, although it may be used if desired. After the reactants have been thoroughly mixed together, an emulsion or cream forms. As the temperature increases from the reaction, gas bubbles are generated bringing about the formation of a cellular material which cures fairly rapidly at room temperature. In certain applications, the physical properties of the foam may be further enhanced by subjecting the foam to moderate heating for several hours. When cured, the foam can be used in a variety of industrial application.

The method of the invention provides several practically desirable advantages in connection with preparation of polyurethane foam. Thus by virtue of the fact that they are derived in part from the chlorine-containing diisocyanates described above, these foams are characterized by a marked reduction in flammability. As such, they are of particular utility in those cushioning and insulating applications which require the use of a cellular plastic material which exhibits a reduced burning rate. Furthermore, this property is achieved, pursuant to the method of the invention, without resort to the use of flame retardant additives or to the use of highly viscous halogenated isocyanate reactants which are difficult to process in foam production. Still further, the foams of the invention have other desirable physical properties, such as high load bearing capacity, which make them particularly suitable for use in such applications as the preparation of mattresses, furniture cushions and the like.

The following examples are provided to illustrate the invention. In these examples, all parts and percentages are by weight unless otherwise specified.

EXAMPLE 1

In a reaction vessel, equipped with a thermometer, a stirrer, a reflux condensor and a nitrogen gas inlet tube, there were placed 966 grams (6 moles) of o-chlorobenzyl chloride, 20 grams of anhydrous aluminum chloride and 2,612 grams (15 moles) of an 80/20 by weight isomer mixture of 2,4-/2,6-toluene diisocyanate. The agitated mixture was heated to 160° C while a slow stream of dry nitrogen gas was passed through it. Hydrogen chloride, which was evolved during the reaction, was removed with the out-flowing nitrogen gas stream, and it was subsequently captured in a separate vessel where it was absorbed in water. After about 6 hours, the evolution of hydrogen chloride ceased. The total yield of this gas was determined, by titration with a base, to represent 67.5% of theory based on complete reaction of the o-chlorobenzyl chloride. Substantially all of the unreacted toluene diisocyanate was removed by distillation. Fractional distillation of the remaining reaction product mixture yielded 865 grams of pure, colorless liquid product distilling at 180°–182° C and 0.5–1.0 mm of mercury pressure. NCO titration of this product gave 27.6% NCO as compared with a calculated theoretical value in o-chlorobenzyl-toluene diisocyanate of 28.1%. The identity and structure of the o-chlorobenzyl-toluene diisocyanate product were confirmed by mass spectrometry (MS), nuclear magnetic resonance (NMR), and vapor phase chromatography (VPC). The analytical tests also showed the presence of several isomers of o-chlorobenzyl-toluene diisocyanate.

The product o-chlorobenzyl-toluene diisocyanate had a measured viscosity at 25° C of 75 cps. The product was allowed to stand for more than 3 months at room temperature and checked again. There was no evidence of any solidification. Rather the product remained all liquid with an unchanged viscosity of 75 cps. at 25° C.

COMPARISON 1 p-chlorobenzyl-toluene diisocyanate was prepared by the same procedure as used in Example 1 except that instead of the o-chlorobenzyl chloride reactant, p-chlorobenzyl chloride was used. The product was initially all liquid of low viscosity. However, on letting this product stand at room temperature for 2 days, a substantial proportion of it solidified.

This comparison is provided to show the drastic and unexpected difference in the product depending on the location of the chlorine on the benzene ring. Thus whereas the o-chlorobenzyl-toluene diisocyanate of the invention is a stable liquid of very low viscosity, the p-chlorobenzyl-toluene diisocyanate is not a stable liquid but exhibits partial solidification on standing.

EXAMPLE 2

The procedure of Example 1 was repeated except that instead of the mixture of 2,4- and 2,6-toluene diisocyanate, 2,4-toluene diisocyanate was used. The o-chlorobenzyl-toluene diisocyanate product had a measured viscosity at 25° C of 108 cps. At the end of three weeks, during which this product was allowed to stand at room temperature, no evidence of solidification was noted. Rather the product remained all-liquid with a viscosity of 108 cps. at 25° C.

COMPARISON 2

The procedure of Example 2 was followed using, instead of o-chlorobenzyl chloride, p-chlorobenzyl chloride. The product p-chlorobenzyl-toluene diisocyanate was a low-viscosity liquid; however, on standing at room temperature overnight, it completely solidified.

EXAMPLE 3

The procedure of Example 1 was used to prepare 2,4-dichlorobenzyl-toluene diisocyanate, using 1,173 grams (6 moles) of 2,4-dichlorobenzyl chloride instead of the 966 grams of o-chlorobenzyl chloride as used in Example 1. The structure and identity of the 2,4-dichlorobenzyl-toluene diisocyanate product were confirmed by MS, NMR, NCO titration and VPC. This product was a stable liquid having a measured viscosity, at 27.7° C, of 373 cps. No evidence of solidification or noticeable increase in viscosity was noted upon storage for more than 11 months at room temperature.

EXAMPLE 4

This example is provided to demonstrate the utility of the o-chlorobenzyl-toluene diisocyanate, product of Example 1, in making polyurethane foam. A flexible foam was prepared using the following ingredients in the indicated proportions

| Ingredients | Parts by Weight |
| --- | --- |
| Oxypropylated glycerin, mol. wt. 3,000 | 100.0 |
| o-chlorobenzyl-toluene diisocyanate | 63.0 |
| Water | 3.0 |
| Triethylene diamine catalyst[1] | 0.60 |
| Stannous octoate | 2.00 |

-continued

| Ingredients | Parts by Weight |
|---|---|
| surfactant[2] | 0.50 |

[1]This catalyst composition, which was purchased commercially under the trademark "Dabco 33-LV", consists essentially of about ⅓ triethylene diamine and about ⅔ dipropylene glycol.
[2]This surfactant, purchased commercially under the trademark "Dow Corning 190", is a block copolymer of a polydimethylsiloxane and a polyether resin.

The above ingredients were hand-mixed and poured into a square cardboard box where foaming commenced instantly. Within about three minutes the foaming reaction was completed and the resulting foam was allowed to cure at room temperature. A stable, uniform cellular product was thus obtained.

EXAMPLE 5

This example is provided to illustrate the utility of o-chlorobenzyl-toluene diisocyanate, in the form of the crude product of the reaction of toluene diisocyanate with o-chlorobenzyl chloride, in making polyurethane foam. Thus the o-chlorobenzyl-toluene diisocyanate had been prepared following the exact procedure of Example 1 except for the following modifications. The total reaction product mixture, including excess toluene diisocyanate, was mixed with 4,459 grams of heptane, and the mixture was allowed to stand overnight at room temperature. As a result, a residue was formed at the bottom. The liquid mixture was syphoned off and thereafter the heptane and unreacted toluene diisocyanate were removed therefrom by distillation. A crude product was thus obtained which contained 80% of o-chlorobenzyl-toluene diisocyanate, the remainder being made up of undistilled reaction by-products.

Following the general procedure of Example 4, a flexible polyurethane foam was prepared using the crude o-chlorobenzyl-toluene diisocyanate and the following other ingredients in the indicated proportions:

| Ingredients | Parts by Weight |
|---|---|
| Polyether polyol [1] | 100 |
| Crude o-chlorobenzyl-toluene diisocyanate | 71 |
| Water | 3 |
| Triethylene diamine catalyst [2] | 1.25 |
| Polydimethyl siloxane surfactant [3] | 0.3 |
| Dow Corning 190 surfactant (as used in Example 4) | 1.0 |

[1] This is a 3,500 molecular weight polyether triol prepared by the oxyalkylation of glycerin with a random mixture consisting of 85% propylene oxide and 15% ethylene oxide.
[2] This is Dabco 33-LV as used in Example 4.
[3] This material, viscosity 5 centistokes at 25° C, was purchased commercially under the trademark "Dow Corning 200".

A uniform, flexible foam product was obtained which was allowed to cure at room temperature. The foam had a core density of 2.5 lbs./cu. ft. Other physical properties of the foam were determined, namely, indentation load deflection properties at 25% and 65% deflection and SAC factor, tensile strength, tear strength and elongation. All these properties were determined in accordance with the test described in ASTM 1564-64T. The tensile strength, expressed in pounds per square inch, is a measure of the minimum tension per unit cross-sectional area which must be exerted on a standard foam sample to cause it to snap or break. The tear strength is expressed in pounds per linear inch, and this indicates the force necessary to cause a one-inch tear in a standard foam sample. Finally the elongation, which is expressed as a percentage of original length of the sample, is a measure of the length that the sample can be stretched to before it breaks or snaps. The results of all these determinations are provided below.

| | |
|---|---|
| Indentation load deflection (lbs.) | |
| at 25% deflection | 45.9 |
| at 65% deflection | 91.8 |
| SAC factor | 2.0 |
| Tensile strength (lbs./sq.in.) | 14 |
| Tear strength (lbs./lin.in.) | 2.3 |
| Elongation (%) | 250 |

What is claimed is:

1. A process for preparing a polyurethane foam from a reaction mixture having from about 0.7 to about 1.25 NCO groups per each OH group, said mixture being comprised of a polyol, a foaming agent, a reaction catalyst and a chlorine-containing methylene-bridged diaryl diisocyanate selected from ortho-chlorobenzyl-toluene diisocyanate and dichlorobenzyl-toluene diisocyanate.

2. The process of claim 1 wherein said polyol is a polyether polyol.

3. A polyurethane foam prepared by the process of claim 2.

4. The process of claim 2 wherein said ortho-chlorobenzyl-toluene diisocyanate is used.

5. A polyurethane foam prepared by the process of claim 4.

6. The process of claim 4 wherein said ortho-chlorobenzyl-toluene diisocyanate is employed in the form of a crude material which is the product of condensing toluene diisocyanate with ortho-chlorobenzyl chloride.

7. A polyurethane foam prepared by the process of claim 6.

8. The process of claim 4 wherein said foam is flexible and said polyether polyol is an oxyalkylated polyhydroxy alcohol having a molecular weight of about 2,500–6,000.

9. A polyurethane foam prepared by the process of claim 8.

10. The process of claim 9 wherein said reaction mixture comprises a silicon-based surfactant.

11. The process of claim 10 wherein said mixture contains about 0.9–1.15 NCO groups per each OH group.

12. The process of claim 11 wherein said catalyst is a tertiary amine, a stannous salt or a mixture thereof.

13. The process of claim 12 wherein said foaming agent is water, and said polyether polyol is oxypropylated glycerin.

14. A polyurethane foam prepared by the process of claim 13.

* * * * *